(12) United States Patent
Konstorum et al.

(10) Patent No.: US 6,171,235 B1
(45) Date of Patent: Jan. 9, 2001

(54) FLEXIBLE PRESSURE RESISTANT COVER FOR THE ARTICULATION SYSTEM OF A MEDICAL INSTRUMENT

(75) Inventors: Gregory Konstorum, Stamford; Ed Grabover, Danbury, both of CT (US)

(73) Assignee: Circon Corporation, Santa Barbara, CA (US)

( * ) Notice: Under 35 U.S.C. 154(b), the term of this patent shall be extended for 0 days.

(21) Appl. No.: 09/087,305

(22) Filed: May 29, 1998

(51) Int. Cl.$^7$ .................................................. A61B 1/005
(52) U.S. Cl. ............................................. 600/139; 600/121
(58) Field of Search ...................................... 600/121, 139, 600/140, 141, 142

(56) References Cited

U.S. PATENT DOCUMENTS

| | | |
|---|---|---|
| 4,327,711 | 5/1982 | Takagi . |
| 4,503,842 * | 3/1985 | Takayama ................................. 128/4 |
| 4,722,210 | 2/1988 | Bourgois et al. . |
| 4,737,153 | 4/1988 | Shimamura et al. . |
| 4,886,049 * | 12/1989 | Darras ........................................ 128/4 |
| 5,005,755 | 4/1991 | Takahashi et al. . |
| 5,125,143 * | 6/1992 | Takahashi ............................... 29/237 |
| 5,201,908 * | 4/1993 | Jones ........................................ 128/4 |
| 5,217,001 * | 6/1993 | Nakao et al. ............................. 128/4 |
| 5,217,468 * | 6/1993 | Clement ................................. 606/127 |
| 5,237,984 * | 8/1993 | Williams, III et al. .................. 128/4 |
| 5,394,864 | 3/1995 | Kobayashi et al. . |
| 5,419,310 * | 5/1995 | Frassica et al. .......................... 128/4 |
| 5,443,057 | 8/1995 | Elmore . |
| 5,547,456 | 8/1996 | Strobl et al. . |
| 5,702,348 * | 12/1997 | Harhen ................................... 600/124 |
| 5,716,322 * | 2/1998 | Hui et al. ............................... 600/133 |
| 5,876,331 * | 3/1999 | Wu et al. ............................... 600/139 |
| 5,928,136 * | 7/1999 | Barry ..................................... 600/142 |
| 5,938,587 * | 8/1999 | Taylor et al. .......................... 600/139 |

OTHER PUBLICATIONS

Abstracts from literature search conducted about Oct., 1997, (4 pages).
*Medical Electronics Technical Bulletin*, Sil–Kore™ Cable Jackets SK–1000, © 1995, W.L. Gore & Associates, Inc. ME–27/10–95.

\* cited by examiner

*Primary Examiner*—John P. Leubecker
(74) *Attorney, Agent, or Firm*—Bradley M. Ganz, Esq.

(57) ABSTRACT

A deflection cover for a medical endoscope comprises a tubular covering that protects the articulation system of an endoscope during sterilization procedures where pressure differentials are generated. The deflection cover is of a single layer of a selected material whose properties provide the deflection cover with adequate flexibility, thinness, and strength for use on a medical endoscope. The deflection cover may include a reinforcement structure, such as a helically oriented thread, to increase the tube's pressure resistance without impeding the tube's longitudinal flexibility, which is needed to allow the articulation system in the endoscope to deflect through its intended range of motion.

16 Claims, 1 Drawing Sheet

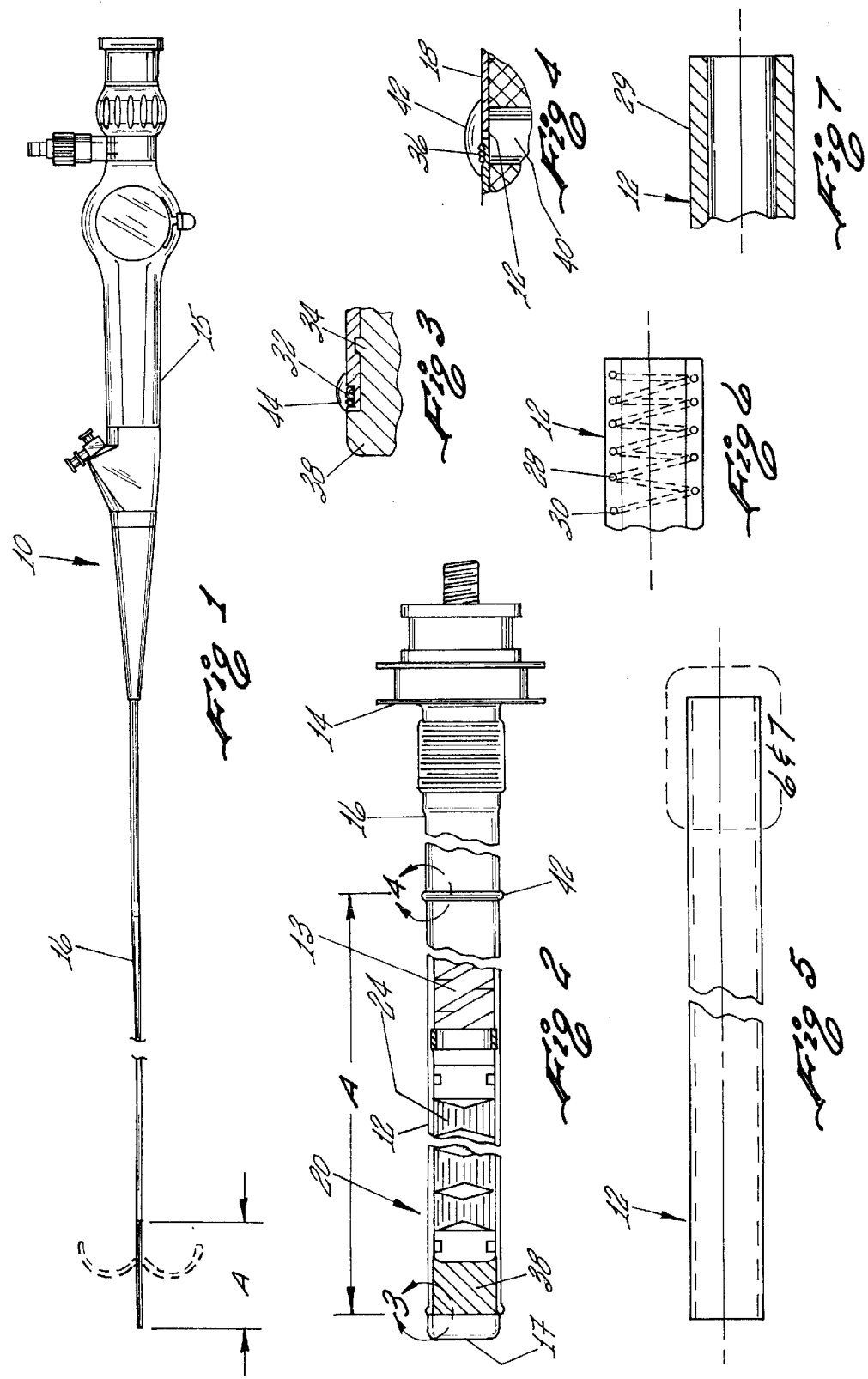

FLEXIBLE PRESSURE RESISTANT COVER FOR THE ARTICULATION SYSTEM OF A MEDICAL INSTRUMENT

BACKGROUND OF THE INVENTION

The present invention relates to a flexible pressure resistant cover, which may be installed on the articulable portion of any flexible endoscope or other medical instrument, which requires a covering of the articulation system.

Medical endoscopes provide a means to view interior areas of the body. To change the direction of view, endoscopes include a mechanical articulation system at their distal viewing end. The proximal end of the endoscope includes means for controlling the articulation system. Endoscopes must be sterilized or disinfected between uses so as not to pass contaminates to patients. Ethylene oxide gas (EtO), Steris, or other systems may be used to sterilize endoscopes. These systems subject an endoscope to significant pressure changes and/or expose the endoscope to fluids that could damage the endoscope's components. In the case of an EtO sterilization system, conventional deflection covers fail starting at about 7 psi pressure differential. These changes and conditions are significant enough that endoscopes typically include a relief valve to prevent failure of the deflection cover and other components.

A person must manually open or close the relief valve, depending on the sterilization procedure. In the open position, the relief valve balances the internal pressure in the endoscope with the external pressure of an EtO sterilization system to preserve the structural integrity of the instrument. In the closed position, the valve keeps harmful fluids from entering the endoscope and damaging endoscope components in a Steris sterilization system.

More particularly, if the valve is not open during EtO sterilization, the cover over the articulation system is prone to rupture, subjecting the internal components of the endoscope to damage. If the valve is not closed during Steris or other cold sterilization procedures, then fluid can enter the instrument to damage the endoscope's internal components. Modern endoscopic instruments can cost thousands of dollars making any damage to them a matter of serious consequence.

It is also desirable to eliminate the relief valves because such valve systems add significantly to the cost of producing an endoscope. The opening and closing of a relief valve also complicates the use of the endoscope.

One attempt to overcome the disadvantages of relief valve-based endoscope system is seen in Kobayashi, et al, and U.S. Pat. No. 5,394,864. The '864 patent describes a cover for the articulable system of an endoscope comprising a pair of inner and outer tubes forming a double-walled tube. A braided tubular material is sandwiched between the inner and outer tube. A second braided tubular material may be disposed between the inner surface of the inner tube and the outer surface of the articulation system.

There are several disadvantages to a deflection cover according to a multiple layer construction. A multiple layer construction adds thickness to the endoscope; thickness is undesirable in minimally invasive surgical procedures. The added thickness may compromise the flex characteristics of the overall structure. An inflexible structure will impede the articulation of the endoscope's tip, rendering it more difficult for a surgeon to view the surgical site.

A multiple layer construction is also more prone to problems such as breakage and delamination during repeated bending cycles of the endoscope tip. Additionally, if the outer layer is damaged, contaminates may become encapsulated between it and an inner layer. Contamination of this nature is difficult to remove. The risk that one of these drawbacks will materialize is heightened by the relatively harsh and demanding nature of the surgical and sterilization environments for the endoscope.

It should be added that the use of a braided material in a deflection cover tube is undesirable because such material not only reinforces by restricting radial flex, but it also restricts longitudinal flex. Longitudinal flex is, in fact, desirable in a deflection cover because it facilitates bending. It is also worth noting that construction of a deflection cover will be simpler and less expensive the fewer layers it has.

For the foregoing reasons, there is a need for a novel and improved endoscopic deflection cover that provides a pressure resistant seal during standard disinfection and sterilization procedures so that relief valves can be eliminated from endoscopes. In addition to providing a pressure resistant seal around the articulation system, the deflection cover must have appropriate flex and wear characteristics, so that the cover does not interfere with the articulation of the endoscope's viewing tip or breakdown under repeated cycles of use. The deflection cover must also be made from medical grade, biocompatible materials that can be inserted into a patient's body without causing trauma, allergic reaction, toxicity, and without carrying harmful biological agents. The deflection cover also should not add unnecessarily to the thickness of the endoscope.

SUMMARY OF THE INVENTION

The present invention overcomes the disadvantages of the prior art by providing a pressure resistant deflection cover with adequate and selectable flex characteristics. The pressure relief valve need not be included on endoscopes incorporating a deflection cover made according to this. It may be based on a single layer of polymer tubing. The single-layer construction enables the thinnest possible profiles for the deflection cover, which is desirable in minimally invasive surgical procedures.

In one embodiment, the deflection cover comprises a tubular covering that includes a reinforcement structure, such as, wire, fiber, thread, or threadlike structures of an appropriate tensile strength. The reinforcement structure is preferably impregnated in the tube and oriented to provide predetermined directional flex characteristics to the deflection cover. In one preferred orientation, the reinforcement structure allows some longitudinal flex in the tube while restricting radial flex. This may be accomplished, for example, by impregnating nylon thread helically around the longitudinal axis of the cover.

In another novel embodiment of the invention, a deflection cover comprising a tubular covering formed from a single layer or wall of material does not require any impregnated thread or other reinforcement structure. Instead, the deflection cover may be based on a single layer of tubing having appropriate material properties. A suitable tubing is SiL-KORE tubing by W. L. Gore.

A deflection cover made according to this invention can withstand pressure differentials typically encountered in conventional EtO sterilization systems. The deflection cover's pressure resistance exceeds 7 psi and is at least as high as 14.7 psi.

To provide a deflection cover with adequate flexibility and minimum wall thickness, it is contemplated for most materials that the ratio of the outer diameter of the cover to the wall thickness be at least about 15. Preferably, the ratio is in the range of about 15 to about 30. To fit commercially available endoscopes the length of the deflection cover should be about 30 mm to about 200 mm. The cover may be adapted to fit endoscopes that may be developed above and below this range as well.

To minimize friction against tissue or other surfaces, and to reduce the risk of hosting microbes or contaminants, the outer surface of the deflection cover should be smooth and non-porous.

The deflection covers of this invention may be attached to an endoscope using conventional bonding techniques.

The foregoing embodiments and additional embodiments are described in more detail in the description and claims that follow and in the attached drawings.

BRIEF DESCRIPTION OF THE DRAWINGS

FIG. 1 is a perspective view of an endoscope with a deflection cover on its distal end.

FIG. 2 is a side view in partial section of the articulation system of an endoscope surrounded by a deflection cover according to the present invention.

FIG. 3 is an enlarged view of circled area 3 in FIG. 2, showing an example means of attaching a deflection cover to an endoscope body.

FIG. 4 is an enlarged view or circled area 4 in FIG. 2, showing an example means of attaching a deflection cover to an endoscope body.

FIG. 5 shows a deflection cover according to the present invention.

FIG. 6 shows a partial side view of one possible embodiment of the deflection cover of FIG. 5, in this case a single-layer deflection cover with a novel reinforcement structure.

FIG. 7 shows a side view of another possible embodiment of a deflection cover of FIG. 5, in this case a deflection made from a single layer of tubing, having material properties as described in the specification.

DETAILED DESCRIPTION OF THE INVENTION

FIG. 1 shows an endoscope 10 with a deflection cover disposed on a distal end portion of a flexible shaft assembly 16, which includes an elongate spiral support spring 13. Viewing end 17 is disposed at the distal end of shaft assembly 16. The endoscope 10 also includes shaft assembly 14 and handle assembly 15 disposed at the proximal end of shaft 16. The handle assembly 15 includes a control assembly (not shown) for deflecting the distal tip of the endoscope, light post assembly for delivering light to the distal tip, and an optics assembly (not shown) for viewing through the endoscope.

The deflection cover surrounds articulation system 20 of the endoscope. The area of flexible shaft assembly 16 where deflection 12 surrounds articulation system 20 is labeled A in FIGS. 1 and 2. Looking at FIG. 2, the articulation system generally comprises linked deflection rings 24, and one or more deflection control cables (not shown) attached to the distal end of the articulation system 20. The cables selectably cause a desired degree of deflection in the articulation system. Commercially available endoscopes have tips that are deflectable up to about 210° from the neutral position of the endoscope tip shown in FIG. 1.

A single-layer deflection cover 12 according to this invention is generally shown in FIG. 5. In one variation of this embodiment shown in FIG. 6, the deflection cover comprises a biocompatible tubular covering 28 impregnated with a reinforcement structure 30 that increases the deflection cover's radial strength. The tubing may be selected from any number of biocompatible tubing materials including fluoroelastomers and polyurethanes. (As used herein "biocompatible" means a medical grade material suitable for use in a medical endoscope.) One suitable tubing material for producing such a deflection cover is 3M FLUOREL FC-2176, available from the Minnesota Mining and Manufacturing company, St Paul, Minn.

Reinforcement structure 30 may comprise a wire, fiber, thread, threadlike, or fibrous structures impregnated in tube 28. In the embodiment of FIG. 6, reinforcement structure 30 is a thread having a tensile strength appropriate to reinforce tubing 28 to a predetermined degree. The thread may be made from various known materials including nylon, steel, or other materials, or combinations of materials that reinforce tubing 28 to a desired strength. The thread 30 should be integrated into the tube to form a unitary structure with the tube. Preferably, thread 30 is impregnated entirely within the wall of the tube to radially reinforce the tube to a desired pressure.

By impregnating the reinforcement structure 30 in tube 28 rather than affixing it to the inner or outer surface, as in prior art multi-layer constructions, the problem of delamination is avoided. This is not to say, however, that an impregnated reinforcement structure according to this invention may never have an exposed portion at an outer or inner surface of the tube to result in a unitary tube construction.

During deflection, one side of tube 28 elongates, and the other side necessarily shortens, as articulation system 20 moves the tube from a linear shape to a deflected, curved shape. Without longitudinal flex capability in the tube to allow for this difference, the tube would impede the articulation system from deflecting the tube through a desired degree of deflection. To avoid this, in one preferred embodiment of this invention, thread 30 is helically oriented in the wall of tube 28 around the longitudinal axis of tube 28, as shown in FIG. 6. Similar such radial orientations are of course possible based on a single thread, multiple threads, and other reinforcement structures, including wires and fibers.

Reinforcement structure 30 may be impregnated into the wall of the tube 28 using conventional coextrusion, molding, or other through other known impregnation processes.

The deflection cover 12 should be produced with appropriate dimensions, material properties, and reinforcement structure to make the cover suitable for use on medical endoscopes, and insertable through conventional insertion channel sizes, which may be as small as 2 mm, or less-as trends continue.

In general, the distal portion of endoscopes range in outer diameter (OD) from about 2 mm to about 15 mm, depending on their purpose. The deflectable portion, i.e., articulation system 20, ranges in length from about 30 mm to about 200 mm. Typically, these sections must be capable of bending up to about 210°. Accordingly, a deflection cover should have an internal diameter (ID) that fits over the OD and length of the articulation system. The cover should not add unnecessary thickness to the OD of the endoscope. The deflection cover 12 has a wall thickness, "T", that is half the difference between the OD and the ID. It is believed that the ratio of outer diameter to thickness (OD/T) should be such that the cover provides adequate strength and flexibility while maintaining a small profile, which is important in microsurgery.

In this regard, it is believed that a suitable ration OD/T is at least about 15. Preferably, the ratio is about 15 to about 30. The ratio may be expressed in terms of French (Fr) sizing where 1 Fr is equivalent to ⅓ mm (0.33 mm). French sizing may be used to size shapes that are not in the form of a circle and consequently do not have a diameter.

The thread diameter may influence wall thickness T. In applications where minimizing T is important, a flat thread or fiber may be used. For example, a 0.003" bonded Dacron may be used in certain applications. By switching to flat stainless steel wire of 0.001", wall thickness T may be reduced by 0.002".

EXAMPLE 1

A 3.5" (inch) length of FLUOREL tubing having an OD of about 5.33, an ID of about 4.87 mm, and a wall thickness T of about 0.23 mm may be used as a deflection cover for an endoscope articulation system. The OD/T equals about 23. A synthetic thread of bonded Dacron having about a 0.1 mm diameter is impregnated into the tube using a conventional coextrusion technique. The thread is oriented in a helical manner with a winding pitch of about 0.013. The FLUOREL tube has a 55+/−5 Shore A Durometer. A deflection cover made in this manner provides suitable flexibility so as not to impede the deflection of a typical endoscope, while having pressure resistance of at least 14.7 psi. The tubing may be tested for pressure resistance as described below.

Persons skilled in the art will recognize the foregoing example may be modified or changed in scale to work on various sized endoscopes. The flexibility and strength can be adjusted as needed by, for example, varying the thickness of the tube, its durometer, and/or the thread type, diameter, and/or the winding pitch.

Another novel embodiment of this invention is a threadless or fiberless deflection cover formed from a single layer of polymer material. SiL-KORE cable jacket materials from W. L. Gore of Phoenix, Ariz. may be used to construct such a single-layer deflection cover 29, as shown in FIG. 7, without the need for an integrated reinforcement material or other materials or structures. A single-layer deflection cover with appropriate pressure resistance and flex characterisics, suitable for use on a medical endoscope may be made from SiL-KORE tubing materials. According to a Gore Technical Bulletin, reportedly from October 1995, the attributes of SiL-KORE tubing include 30% elongation, tensile strength of 6,000 psi, flexibility of 80 gm/cm, cut-through resistance of about 32 lbs, load sharing modulus (secant modulus) of 54,044.3, tensile elongation of 16.5% @ 71.5 lbs, high lubricity, high hoop strength, MRI compatible, autoclavable, and biocompatible. Until the present invention, SiL-KORE materials have not previously been used to make deflection covers for medical endoscopes. The Gore Technical Bulletin only reports that the material has been used in medical interconnects, fiber optic buffering tubes, and fine wire sensing leads.

An example of a deflection cover according to this invention engineered from SiL-KORE tubing is described in following Example 2.

EXAMPLE 2

A 3.5" (inch) length of SiL-KORE SK-1000 tubing having an OD of about 5.33, an ID of about 4.87 mm, and a wall thickness T of about 0.23 mm may be used as a deflection cover for an endoscope articulation system. The tubing has about a 55 Shore A durometer. The OD/T equals about 23. A deflection cover made according to this embodiment provides suitable flexibility so as not to interfere with the deflection of a typical endoscope, while having a pressure resistance of at least 14.7 psi. The tubing may be tested for pressure resistance as described below.

A deflection cover made in accordance with Example 1 or 2 may be used to replace the conventional deflection cover on a standard medical endoscope without impeding the endoscope's original range of deflection. For example, an ACN-1 CystoNephroscope, available from Circon ACMI of Stamford, Conn., deflects up to about 180° with its conventional deflection cover of FLUOREL tubing. The conventional FLUOREL deflection cover has a pressure resistance of about 7 psi. When an ACN-1 endoscope is refitted with a deflection cover of Example 2, 180° of deflection is still easily achieved. However, unlike the stock deflection cover, the deflection cover of Example 2 is sufficiently pressure resistant that, the pressure relief valve may be omitted from the endoscope in EtO systems.

To test a deflection cover for whether it is pressure resistant at a specified pressure, one end of about a 3" length of deflection cover tube may be attached to a pump port. The other end is sealed by, for example, plugging, clamping, or tying. The tube is inflated to a desired pressure.

A convenient pressure standard for the embodiments discussed herein is about 14.7 psi for 10 minutes. This corresponds to about the maximum pressure differential in an EtO sterilization system. The present invention may also be tested at any other specified pressure. For example, it may be tested at lower pressures or higher pressures, depending on the particular sterilization system or the settings for a particular sterilization system. An EtO sterilization system, or other system, for example, might operate, or be set to operate, to produce at pressure differential of less than 14.7 psi (the theoretical maximum pressure differential in an EtO system), e.g., 9 psi, 12 psi, or about 13.8 psi (the maximum actual pressure differential in an EtO system).

When placed under the desired pressure, deflection cover tube must not burst or change shape excessively during the time it is holding the pressure. If it bursts, it is not pressure resistant at the specified pressure. A tube whose size changes so much that its function is impaired, or whose size changes so much that a larger insertion channel for the endoscope is required, is not pressure resistant at the specified pressure. If the outer diameter expands more than about 7% of its original OD, this may be generally considered an excessive size change.

A water bath may be used to evaluate the tube for leaks. In this evaluation, the tube is inflated to about 5 psi. If bubbles are visible to the naked eye, the tube is not pressure resistant.

Accordingly, for purposes of this invention, a deflection cover is not pressure resistant at a specified pressure if it bursts, leaks, or changes shape excessively at a specified pressure.

In the foregoing embodiments, it is advantageous to have the outer surface of the deflection cover be non-porous and smooth so that it is atraumatic, low friction, and less likely to carry contaminants or infectious agents into a patient's body.

The foregoing tubing embodiments may be attached to flexible shaft assembly 16 and other components of the endoscope using, for example, standard cementing or bonding techniques known to persons skilled in the art. As shown in FIGS. 2–4, the deflection cover 12 is attached at its distal end to the endoscope's objective tip 38. Ridge 34 helps secure the position of the deflection cover. The proximal end of the deflection cover is attached to the rigid end section of shaft assembly 40, proximally adjacent flexible shaft cover tube 18. In addition to chemical bonding agents, attachment means 32 and 36 may be included to help bind the ends of deflection cover to the endoscope. The attachment means may comprise a thread, such as a 0.003" Dacron thread wrapped over and around the ends of the deflection cover. Bands 42 and 44, formed of epoxy for example, are disposed over the attachment means 32 and 36 to seal them and reinforce the binding. The attachment method must also be suitable for the intended environment of the endoscope e.g., EtO or Steris sterilization systems.

Persons skilled in the art will recognize the foregoing examples are not limitations but examples that may be modified or changed in scale or properties to work on endoscopes of various sizes and types. For instance, the flexibility and strength properties can be adjusted as needed by, for example, varying the thickness of the tube, its durometer, and/or the thread type, diameter and/or the winding pitch. While this invention has generally been described in terms of endoscopes, it will be recognized that the teachings herein generally applies to any other medical instrument with a deflectable portion.

What is claimed is:

1. A deflection cover for the articulable portion of a medical instrument comprising:
    a tubular covering for surrounding the articulation system of a medical instrument, the tubular covering having a pressure resistance of at least about 9 psi, and being composed of a biocompatible material having a ratio of OD/T of at least about 15; and wherein the tubular covering comprises a reinforcement structure that radially strengthens the tube to enable the tubular covering to have a pressure resistance of at least about 14 psi.

2. The deflection cover of claim 1 wherein the reinforcement structure renders the deflection cover more expandable in the longitudinal dimension than the radial dimension.

3. The deflection cover of claim 2 wherein the reinforcement structure comprises a thread impregnated in the tubular covering in a radial orientation.

4. The deflection cover of claim 3 wherein the thread is helically oriented in the tubular covering.

5. The deflection cover of claim 1 wherein the reinforcement structure comprises a fibrous material impregnated in the tubular covering.

6. An endoscope having an articulation system at its distal portion, the articulation system being surrounded by a deflection cover comprising a single-layer tubular covering, the single layer of material being impregnated with a radially strengthening reinforcement structure, the deflection cover capable of withstanding a pressure differential of at least about 9 psi.

7. The endoscope of claim 6 wherein the radially strengthening reinforcement structure impregnated in the single layer of material comprises a radially oriented thread.

8. The endoscope of claim 7 wherein the radially oriented thread is in the form of a helix.

9. The endoscope of claim 6 wherein the reinforcement structure renders the deflection cover more expandable in the longitudinal dimension than the radial dimension.

10. The endoscope of claim 6 wherein the tubular covering has a non-porous outer surface.

11. The endoscope of claim 6 wherein the ratio of OD/T is at least about 15.

12. A deflection cover for the articulable portion of an endoscope comprising:
    a tubular covering for surrounding the articulable portion, the tubular covering having a ratio of OD/T of at least about 15, the tubular covering comprising a biocompatible polymer material having a pressure resistance of at least about 9 psi, the tube being deflectable to at least about 45°, and
    wherein the deflection cover includes a reinforcement structure that radially strengthens the tube.

13. The deflection cover of claim 12 wherein the reinforcement structure is helically oriented in the tubular covering.

14. An endoscope having an articulation system at its distal portion, the articulation system being surrounded by a deflection cover comprising a tubular covering composed of a single layer of biocompatible material having a pressure resistance of at least about 9 psi, wherein a radially strengthening reinforcement structure is impregnated in a single layer of material.

15. The endoscope of claim 14 wherein the reinforcement structure renders the deflection cover more expandable in the longitudinal dimension than the radial dimension.

16. The endoscope of claim 15 wherein the tubular covering comprises a polymer with a non-porous outer surface.

* * * * *